(12) United States Patent
Hsieh et al.

(10) Patent No.: US 8,552,180 B2
(45) Date of Patent: Oct. 8, 2013

(54) METHOD FOR SEPARATING AMIDE FROM AMINO ACID IONIC LIQUID

(75) Inventors: Cheng-Fa Hsieh, Taipei (TW); Chien-Chuan Shih, Taipei (TW); Chi-Yuan Chen, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 550 days.

(21) Appl. No.: 12/637,190

(22) Filed: Dec. 14, 2009

(65) Prior Publication Data

US 2011/0105793 A1 May 5, 2011

(30) Foreign Application Priority Data

Oct. 30, 2009 (TW) .............................. 98136832 A

(51) Int. Cl.
*C07D 201/04* (2006.01)
(52) U.S. Cl.
USPC ........... 540/535; 540/484; 540/534; 562/553; 562/573
(58) Field of Classification Search
USPC ........... 540/534, 384, 535, 485; 562/553, 573
See application file for complete search history.

(56) References Cited

U.S. PATENT DOCUMENTS

| | | | |
|---|---|---|---|
| 3,694,433 A | 9/1972 | Beckham | |
| 3,912,721 A | 10/1975 | Mattone et al. | |
| 3,944,543 A | 3/1976 | Goettsch et al. | |
| 4,013,640 A | 3/1977 | Somekh | |
| 4,036,830 A | 7/1977 | de Rooij et al. | |
| 4,328,154 A | 5/1982 | Senni et al. | |
| 6,111,099 A | 8/2000 | Frentzen et al. | |

FOREIGN PATENT DOCUMENTS

| | | | |
|---|---|---|---|
| CN | 1670017 A | | 9/2005 |
| CN | 1852898 A | | 10/2006 |
| CN | 1919833 | * | 2/2007 |
| CN | 1919834 A | | 2/2007 |
| JP | 2003104969 | * | 4/2003 |
| WO | WO 2005/028446 | * | 3/2005 |
| WO | WO-2008/145312 A1 | | 12/2008 |

OTHER PUBLICATIONS

English translation of WO 2005/028446, 2005.*

* cited by examiner

*Primary Examiner* — Shailendra Kumar
(74) *Attorney, Agent, or Firm* — Edwards Wildman Palmer LLP; Peter F. Corless, Esq.; Richard B. Emmons

(57) ABSTRACT

The present invention provides a method for separating an amide from an amino acid ionic liquid. The method includes the step of providing a polar solvent and an extracting agent to the amino acid ionic liquid, so as to separate the amide from the amino acid ionic liquid. In the method of the present invention, there is no need to add ammonium for neutralization, such that no byproduct, ammonium sulfate, is formed. In addition, after the amide is separated from the amino acid ionic liquid, the amino acid ionic liquid can be recycled.

18 Claims, No Drawings

METHOD FOR SEPARATING AMIDE FROM AMINO ACID IONIC LIQUID

CROSS-REFERENCES TO RELATED APPLICATIONS

This application claims under 35 U.S.C. §119(a) the benefit of Taiwanese Application No. 098136832 filed Oct. 30, 2009 the entire contents of which is incorporated herein by reference.

BACKGROUND OF THE INVENTION

1. Field of the Invention

The present invention relates to a method for preparing amides, and more particularly, to a method for separating an amide from an amino acid ionic liquid.

2. Description of the Prior Art

Caprolactam is an important raw material in the manufacture of nylon 6 fibers and thin films. Beckman rearrangement of cyclohexanone oxime is an important reaction step in producing caprolactam. Currently, oleum is used as a catalyst for converting cyclohexanone oxime to caprolactam sulfate during Beckman rearrangement, and then ammonia is used for neutralization, so as to obtain caprolactam. While the conversion rate of cyclohexanone oxime is almost 100% and the selectivity for caprolactam is 99%, a large amount of low-valued ammonium sulfate is generated during the reaction, and concentrated sulfuric acid used for catalysis causes problems such as corrosion to the whole equipment and environmental pollution. In the recent years, researches on new production technologies of caprolactam focus on reducing or avoiding the generation of the by-product, ammonium sulfate. Moreover, compared with the gas phase reaction, liquid-phase rearrangement has advantages including moderate reaction conditions, fewer requirements to the equipments, etc., and is advantageous to the reconstruction of the current equipments. As a result, scholars worldwide have put efforts on developing liquid-phase rearrangement, and attained substantial developments and breakthrough. For example, in Chinese Patent No. 1852898A assigned to Sumitomo Chemical Company Ltd. in Japan, an ionic liquid having the sulfonate group is used as a catalyst to give the selectivity of caprolactam up to 99%. In Chinese Patent No. 1919834 assigned to Lanzhou Institute of Chemical Physics in China, an ionic liquid having sulfuryl chloride is used as a catalyst to give the selectivity of caprolactam up to 97.2%. In WO2008/145312A1 assigned to DSM N.V. in Netherlands, an anionic solution having sulfate is used for conversion reaction to give the selectivity of amide up to 99%.

In addition, it has been disclosed that in the rearrangement reaction with oleum, sulfuric acid is neutralized with an alkaline, and then caprolactam is extracted by an organic solvent. For example, in U.S. Pat. Nos. 3,944,543, 4,036,830 and 3,694,433, an amide is extracted to an organic solvent by the solvent including an arylalkyl, haloakyl and alcohol, so as to be further purified. U.S. Pat. Nos. 4,328,154, 4,013,640 and 3,912,721 disclose extracting an amide by a solvent, alkylphenol. In U.S. Pat. No. 6,111,099, nylon 6 is depolymerized, caprolactam is recovered by extraction with alkyl phenolic compounds, wherein the alkyl is $C_{6-25}$ alkyl, and the caprolactam and alkyl phenolic compounds are recovered by distillation.

In the recent years, due to the concepts of atom economy and environmental economy, ionic liquids are widely applied in academia and industry. Particularly, it is developed to use the ionic liquids are in a rearrangement reaction of cyclohexanone. For example, Chinese Patent No. 1670017 discloses that Beckman rearrangement is performed with an ionic liquid and a catalyst system including a phosphorus compound. However, the acidic phosphorus compounds are easily coupled to the products of the rearrangement reaction, such that the products of the rearrangement reaction are in the ionic liquid phase rather than in the organic solvent, resulting in very low efficiency of extraction by a solvent or vacuum distillation. Although the products can be separated by neutralization with ammonium, the addition of ammonium results in the formation of ammonium sulfate, which needs to be avoided in industry.

The above-mentioned techniques have high conversion rate of ketoximes and high selectivity of amides, but the rearrangement reaction with non-oleum is hard to be used in industry due to the above drawbacks. Specifically, caprolactam cannot be separated from the rearrangement reaction system. In other words, it is the barrier in eliminating byproduct ammonium sulfate that amides need to be separated from a liquid phase in Beckman rearrangement reaction.

Hence, it is a need to develop a method for separating products from Beckman rearrangement reaction and recycling the ionic liquid in industry.

SUMMARY OF THE INVENTION

The present invention provides a method for separating an amide from an amino acid ionic liquid in Beckman rearrangement reaction, and the method includes the step of providing a polar solvent and an extracting agent to the amino acid ionic liquid, so as to separate the amide from the amino acid ionic liquid. The polar solvent is one selected from the group consisting of water, $C_{1-6}$ aliphatic alcohols, acetonitrile, tetrahydrofuran, N,N-dimethylformamide, dimethyl sulfoxide, N-methylpyrollidone and the combination thereof. The extracting agent is one selected from the group consisting of benzene, toluene, xylene, $C_{4-8}$ aliphatic alcohols, alkyl phenols, ketones, esters, ethers and the combination thereof.

In the method of the present invention, ketoximes are catalyzed in Beckman rearrangement reaction in the presence of an amino acid anion liquid to produce amides, a polar solvent is added to destroy the interaction between the amides and the ionic liquid, and the amides are separated from the ionic liquid by an extracting agent. Therefore, in comparison with the conventional methods, there is no volatile compound produced, no need to add ammonium for neutralization, and no byproduct (ammonium sulfate) produced, such that the ionic liquid can be recycled. Moreover, the conversion rate of ketoximes and selectivity of amides are high, and there is no need to add cocatalysts in the method of the present invention. Accordingly, the method of the present invention is suitable for large scale productions in industry.

DETAILED DESCRIPTION OF THE INVENTION

The following specific embodiments are provided to illustrate the disclosure of the present invention. These and other advantages and effects can be easily understood by those skilled in the art after reading the disclosure of this specification.

The present invention provides a method for separating an amide from an amino acid ionic liquid in Beckman rearrangement reaction, and the method includes the step of providing a polar solvent and an extracting agent to the amino acid ionic liquid, so as to separate the amide from the amino acid ionic liquid.

According to the method of the present invention, in the catalysis system including an amino acid ionic liquid, an organic solvent, and optionally a Bronsted acid, a ketoxime is catalyzed to produce an amide. The amino acid ionic liquid includes an anion selected from an inorganic acid group and an organic acid group of a Bronsted acid, and a cation of formula (I)

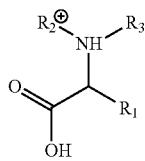

(I)

wherein $R_1$ and $R_2$ are independently hydrogen or $C_{1-8}$alkyl, $R_1$ and $R_2$ are identical or different, and $R_3$ is hydrogen, cycloimino or $C_{1-8}$alkyl, in which the $C_{1-8}$alkyl is unsubstituted or substituted by a substituent selected from the group consisting of hydroxyl (—OH), carboxyl (—COOH), guanidine (NH$_2$C(=NH)NH—), amino (—NH$_2$), amido (—CONH$_2$), ester group (—COOR), sulfonate (—SO$_3$H), chlorosulfinyl (ClSO—), hydroxyphenyl, $C_{1-8}$alkylthio, thiol (—SH), $C_{6-10}$aryl and 5- to 10-membered heteroaryl. More specifically, the amino acid ionic liquid and the Bronsted acid are shown as formula (II):

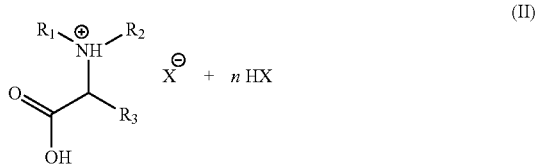

(II)

wherein HX is the Bronsted acid, X is the anion of the Bronsted acid selected from the group consisting of sulfurate, phosphorate, acetiate, methylsulfonate, trifluoromethylsulfonate, trifluoroacetate, hexafluorophosphorate, fluoroborate, and a combination thereof, and n is an integer from 0 to 100, and preferably from 0 to 15.

Generally, a molar ratio of the cation of the amino acid ionic liquid to the anion of the ketoxime is in a range from 100:1 to 1:100, and preferably from 10:1 to 1:10.

In a preferred embodiment, the anion of the amino acid ionic liquid is sulfate.

In a preferred embodiment, $R_1$ and $R_2$ are independently $C_{1-8}$alkyl, $R_3$ is a $C_{1-8}$alkyl substituted by carboxyl (—COOH), guanidine (NH$_2$C(=NH)NH—), amino (—NH$_2$), amido (—CONH$_2$) or hydroxyphenyl. Further, the Bronsted acid can be a mono-acid or a mixture of acids.

Generally, the Bronsted acid can be, but not limited to, sulfuric acid, phosphoric acid, acetic acid, methylsulfonic acid, trifluoromethylsulfonic acid, trifluoroacetic acid, hexafluorophosphoric acid, fluoroboric acid, and a combination thereof.

The term "$C_{1-8}$alkyl" used herein refers to straight, branched, or cyclic alkyl. The $C_{1-8}$alkyl can be, but not limited to, methyl, ethyl, propyl, isopropyl, butyl, sec-butyl, pentyl, hexyl and cyclohexyl, wherein methyl, ethyl, propyl, butyl and pentyl are preferable.

In the present invention, the ketoxime for preparing an amide is one selected from the group consisting of acetone oxime, butanone oxime, benzophenone oxime, acetophenone oxime, cyclopentanone oxime, cyclohexanone oxime, cycloheptanone oxime, cyclooctanone oxime and cyclododecanone oxime. In a preferred embodiment, the ketoxime is cyclohexanone oxime.

In a preferred embodiment of the present invention, the amino acid ionic liquid is one selected from the group consisting of a glycine sulfuric acid-ionic liquid, an isoleucine sulfuric acid-ionic liquid, an arginine sulfuric acid-ionic liquid, a glutamic acid sulfuric acid-ionic liquid, a tyrosine sulfuric acid-ionic liquid, an aspartic acid sulfuric acid-ionic liquid, a lysine sulfuric acid-ionic liquid, a threonine sulfuric acid-ionic liquid, a phenylalanine sulfuric acid-ionic liquid, a serine sulfuric acid-ionic liquid and a combination thereof. More preferably, the amino acid ionic liquid is an isoleucine sulfuric acid-ionic liquid, N,N-dimethylglutamic acid sulfate, N,N-dimethylaspartic acid sulfate, N-methylglutamic acid sulfate or N-methylaspartic acid sulfate. In a preferred embodiment of the present invention, the amino acid ionic liquid is one mole of N,N-dimethylglutamic acid sulfate liquid or glutamic acid sulfuric acid-ionic liquid. In addition, one or more amino acid ionic liquids can be used in the present invention.

In the method of the present invention, an amino acid ionic liquid, an organic solvent and a Bronsted acid are mixed to form a two-phase catalyst system at a rearrangement temperature, a ketoxime is dissolved in the organic solvent to be added into the two-phase catalyst system for a rearrangement reaction, and after the reaction is terminated and the two phase are formed, the organic solvent phase is removed. Then, a polar solvent and an extracting agent are added into the ionic liquid phase. Upon stirring and extraction, the extract phase having the amide and the ionic liquid phase are formed. The amide is further purified, the polar solvent is removed from the ionic liquid phase by distillation, and the ionic liquid is further recycled, such that the amide is separated from the ionic liquid.

In the method of the present invention, an amino acid ionic liquid, an organic solvent and a Bronsted acid are mixed to form a two-phase catalyst system. The organic solvent is an aromatic hydrocarbon, which can be benzene, toluene, xylene or a combination thereof. In a preferred embodiment, the organic solvent is toluene.

In the present invention, the polar solvent is one selected from the group consisting of water, $C_{1-6}$aliphatic alcohols, acetonitrile, tetrahydrofuran, N,N-dimethylformamide, dimethyl sulfoxide, N-methylpyrollidone and the combination thereof. Preferably, the polar solvent is water. The extracting agent of the present invention is one selected from the group consisting of a hydrocarbon, an alkyl phenol, a $C_{4-8}$aliphatic alcohol, a ketone, an ester, an ether and a combination thereof. The hydrocarbon is benzene, toluene or xylene. The $C_{4-8}$aliphatic alcohol is butanol, isobutanol, tert-butyl alcohol, propanol, isopropanol, hexanol, heptanol, octanol, 2-etyl-1-hexanol, dimethylbutanediol or cyclohexanol. The alkyl phenol is a mono-substituted phenol having at least three carbon atoms or a di-substituted phenol having at least three carbon atoms, such as 2-tert-butylphenol, or 2-isopropylphenol. The ketone is 2-pentanone, 2-hexanone, 2-heptanone, methyl isobutyl ketone or 2,4-pentanedione. The ester is ethyl acetate, methyl butyrate or methyl valerate. The ether is ethyl ether, butyl ether or isopropyl ether. In an embodiment of the present invention, the extracting agent is 2-tert-butylphenol.

Generally, while a ketoxime is catalyzed in an amino acid anionic liquid and Beckman rearrangement reaction to produce an amide, a molar ratio of the amino acid anionic liquid to the ketoxime is in a range from 1:10 to 10:1, and preferably 1:1 to 5:1. The reaction is performed at a temperature ranging from 60 to 150° C., preferably from 80 to 130° C., and more preferably from 90 to 120° C. The reaction is performed for 0.1 to 10 hours, preferably from 0.5 to 3 hours, and more preferably from 0.5 to 1 hour.

In addition, while the polar solvent and the extracting agent are added to separate the amide from the amino acid ionic liquid, the weight ratio of the polar solvent to the amino acid ionic liquid is in a range from 10:1 to 1:50, preferably from 4:1 to 1:20, and more preferably from 4:1 to 1:5. The weight ratio of the extracting agent to the amino acid ionic liquid is in a range from 10:1 to 1:2, preferably from 6:1 to 1:1, and more preferably from 3:1 to 1:1.

EMBODIMENTS

The present invention is illustrated by, but not limited to, the following embodiments. Ketoximes and amides were measured by gas chromatography. The conversion rate of ketoximes and selectivity of amides were calculated by the following equations.

Conversion rate (%)=(mole number of reacted ketoxime/mole number of original ketoxime (%)]×100%

Selectivity (%)=[mole number of the resulting amide/mole number of reacted ketoxime (%)]×100%

The extract efficiency of amides was calculated by the following equation.

Extract efficiency (%)=[mole number of the extracted amide/mole number of amide]×100%

In the following embodiments, the conversion rates of ketoximes in the amino acid anionic liquid before extraction were all more than 99.2%, and the selectivities of amides were all more than 85%. Particularly, while 2-tert-butylphenol was used as an extracting agent, the conversion rate of cyclohexanone oxime was more than 99.99% and the selectivity of caprolactam was 97.13%.

Embodiments 1-9

In each Embodiment, 100 ml of toluene and 0.01 mole of glutamic acid sulfuric acid-ionic liquid having excess sulfuric acid were added into a 250 ml round-bottom flask. The mixture was stirred with a magnetic bar. After the temperature of the mixture reached 110° C., 0.002 mole of cyclohexanone oxime was added into the mixture, wherein the molar ratio of the amino acid ionic liquid to the ketoxime was 5:1. The reaction was performed for 0.5 hour, and then the toluene phase was removed after the mixture was cool down. 15 g of water and 7.42 g f the extracting agent illustrated in Table 1 were added into the mixture. The mixture was stirred at 60° C. for 5 minutes, and placed in the separating funnel for stratification. The toluene phase was collected. The above extraction steps were repeated twice. The toluene phase was analyzed by gas chromatography. The ionic liquid phase was further extracted with each 30 ml of chloroform for several times until almost no caprolactam was measured by gas chromatography in the ionic liquid. The results are shown in Table 1.

TABLE 1

| Embodiment | Extracting agent | Extract efficiency (%) |
|---|---|---|
| 1 | 2-tert-butylphenol | 98.31 |
| 2 | 2-iso-propylphenol | 99.70 |
| 3 | ethyl acetate | 46.93 |
| 4 | cyclohexane | 9.12 |
| 5 | methyl isobutyl ketone | 44.24 |
| 6 | 2-heptanone | 39.59 |
| 7 | 1-pentanol | 90.41 |
| 8 | 1-octanol | 78.13 |
| 9 | 2-methyl-2-butanol | 86.03 |

Comparative Examples 1-4

The steps as those in Embodiment 1 were performed except that the extracting agent listed in Table 2 was used, and the polar solvent, water, was not used. The results are shown in Table 2.

TABLE 2

| Comparative example | Extracting agent | Extract efficiency (%) |
|---|---|---|
| 1 | ethyl acetate | 2.39 |
| 2 | cyclohexane | 0.03 |
| 3 | methyl isobutyl ketone | 0.02 |
| 4 | 2-heptanone | 4.71 |

According to Tables 1 and 2, the reaction performed with the extracting agent but no polar solvent such as water had significantly lower extract efficiency.

Embodiments 10-14

In each Embodiment, 150 ml of toluene and 0.05 mole of glutamic acid sulfuric acid-ionic liquid having excess sulfuric acid were added into a 250 ml round-bottom flask. The mixture was stirred with a magnetic bar. After the temperature of the mixture reached 110° C., 0.03 mole of cyclohexanone oxime was added into the mixture, wherein the molar ratio of the amino acid ionic liquid to the ketoxime was 5:3. The reaction was performed for 0.5 hour, and then the toluene phase was removed after the mixture was cool down. The water illustrated in Table 3 and 37.10 g of 2-tert-butylphenol were added into the mixture. The mixture was stirred at 60° C. for 5 minutes, and placed in the separating funnel for stratification. The extracting agent phase was collected and analyzed by gas chromatography. The ionic liquid phase was further extracted with each 30 ml of chloroform for several times until almost no caprolactam was measured by gas chromatography in the ionic liquid. The conversion rates of the reactants, the selectivities of the products and the extract efficiency of the extracting agents were calculated. The results are shown in Table 3.

Comparative Example 5

The steps in Embodiment 10 were repeated except the addition of water. The results are shown in Table 3.

TABLE 3

| | Water (g) | Extract efficiency (%) |
|---|---|---|
| Embodiment 10 | 18.55 | 99.80 |
| Embodiment 11 | 9.28 | 96.79 |
| Embodiment 12 | 7.42 | 91.16 |
| Embodiment 13 | 5.57 | 87.62 |
| Embodiment 14 | 3.71 | 76.22 |
| Comparative example 5 | 0 | 31.93 |

As shown in Table 3, Embodiments 10-11 using the polar solvent had significantly higher extract efficiency than Comparative example 5, which used no polar solvent.

Embodiments 15-19

In each Embodiment, 150 ml of toluene and 0.05 mole of glutamic acid sulfuric acid-ionic liquid having excess sulfuric acid were added into a 250 ml round-bottom flask. The mixture was stirred with a magnetic bar. After the temperature of the mixture reached 110° C., 0.01 mole, 0.02 mole, 0.03 mole, 0.04 mole and 0.05 mole of cyclohexanone oxime were respectively added into the mixture, wherein the molar ratio of the amino acid ionic liquid to the ketoxime was shown in Table 4. The reaction was performed for 0.5 hour, and then the toluene phase was removed after the mixture was cool down. 9.28 g of water and 37.10 g of 2-tert-butylphenol were added into the mixture. The mixture was stirred at 60° C. for 5 minutes, and placed in the separating funnel for stratification. The above extraction steps were repeated twice. The extracting agent phase was collected and analyzed by gas chromatography. The ionic liquid phase was further extracted with each 30 ml of chloroform for several times until almost no caprolactam was measured by gas chromatography in the ionic liquid. The conversion rates of the reactants, the selectivities of the products and the extract efficiency of the extracting agents were calculated. The results are shown in Table 4.

TABLE 4

| Embodiment | Ionic liquid:ketoxime (molar ratio) | Extract efficiency (%) |
|---|---|---|
| 15 | 5:1 | 96.79 |
| 16 | 5:2 | 96.56 |
| 17 | 5:3 | 97.73 |
| 18 | 5:4 | 98.22 |
| 19 | 5:5 | 97.28 |

Embodiments 20-22

In each Embodiment, 150 ml of toluene and 0.05 mole of glutamic acid sulfuric acid-ionic liquid having excess sulfuric acid were added into a 250 ml round-bottom flask. The mixture was stirred with a magnetic bar. After the temperature of the mixture reached 110° C., 0.03 mole of cyclohexanone oxime was added into the mixture, wherein the molar ratio of the amino acid ionic liquid to the ketoxime was 5:3. The reaction was performed for 0.5 hour, and then the toluene phase was removed after the mixture was cool down. 8.58 g of water and 2-tert-butylphenol were added into the mixture (this step was repeated for three times, and the total amount of the extracting agent was shown in Table 5). The mixture was stirred at 60° C. for 5 minutes, and placed in the separating funnel for stratification. The extraction steps were repeated twice. The extracting agent phase was collected and analyzed by gas chromatography. The ionic liquid phase was further extracted with each 30 ml of chloroform for several times until almost no caprolactam was measured by gas chromatography in the ionic liquid. The conversion rates of the reactants, the selectivities of the products and the extract efficiency of the extracting agents were calculated. The results are shown in Table 5.

Comparative Example 6

The steps in Embodiments were repeated except the addition of water, and the amount of the extracting agent was twice of the ionic liquid. The results are shown in Table 5.

TABLE 5

| | Extracting agent (g) | Extract efficiency (%) |
|---|---|---|
| Embodiment 20 | 37.10 | 85.90 |
| Embodiment 21 | 18.55 | 67.29 |
| Embodiment 22 | 9.28 | 52.57 |
| Comparative example 6 | 37.10 | 31.93 |

As shown in Table 5, the extract efficiency in Comparative example 6 without using a polar solvent is low even though high amount (37.10 g) of the extracting agent was used.

Embodiments 23-26

In each Embodiment, 150 ml of toluene and 0.05 mole of glutamic acid sulfuric acid-ionic liquid having excess sulfuric acid were added into a 250 ml round-bottom flask. The mixture was stirred with a magnetic bar. After the temperature of the mixture reached 110° C., 0.03 mole of cyclohexanone oxime was added into the mixture, wherein the molar ratio of the amino acid ionic liquid to the ketoxime was 5:3. The reaction was performed for 0.5 hour, and then the toluene phase was removed after the mixture was cool down. As shown in Table 6, 0.86 g of the polar solvent and 8.58 g of 2-tert-butylphenol were added into the mixture. The mixture was stirred at 60° C. for 5 minutes, and placed in the separating funnel for stratification. The extraction steps were repeated twice. The extracting agent phase was collected and analyzed by gas chromatography. The ionic liquid phase was further extracted with each 30 ml of chloroform for several times until almost no caprolactam was measured by gas chromatography in the ionic liquid. The conversion rates of the reactants, the selectivities of the products and the extract efficiency of the extracting agents were calculated. The results are shown in Table 6.

TABLE 6

| Embodiment | Polar solvent | Extract efficiency (%) |
|---|---|---|
| 23 | methanol | 93.99 |
| 24 | ethanol | 85.00 |
| 25 | propanol | 85.62 |
| 26 | isopropanol | 97.86 |

According to the above results, the present invention provides the two-phase catalysis system including the amino acid ionic liquid and the organic solvent (and optionally Bronsted acid), in which Beckman rearrangement reaction of ketoximes is performed to produce amides, and high conversion rate of ketoximes and high selectivity of amides are obtained. In the present invention, the polar solvent and the extracting agent are added into the amino acid ionic liquid, the extracting agent phase having amides and the ionic liquid phase are formed upon stirring, and the amides are separated from the extracting agent phase and subjected to the subsequent purification process, such that the amides are separated from the ionic liquid. Moreover, there is no volatile compound formed in the method of the present invention, and there is no need to add ammonium during extraction, such that there is no byproduct, ammonium sulfate. In addition, the ionic liquid can be recycled, such that the method of the present invention causes no pollution, saves energy and resources, and has a promising prospect in industrial applications.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A method for separating an amide from an amino acid ionic liquid in Beckman rearrangement reaction, comprising the steps of:
    catalyzing a ketoxime in the Beckman rearrangement reaction in the presence of the amino acid ionic liquid, the organic solvent and a Bronsted acid to produce the amide; and
    providing a polar solvent and an extracting agent to the amino acid ionic liquid, so as to separate the amide from the amino acid ionic liquid,
    wherein the amino acid ionic liquid comprises an anion selected from an inorganic acid group and an organic acid group of the Bronsted acid, and a cation of formula (I):

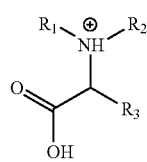

(I)

wherein $R_1$ and $R_2$ are independently hydrogen or $C_{1-8}$alkyl, and $R_3$ is hydrogen, cycloimino, or $C_{1-8}$alkyl, wherein the $C_{1-8}$alkyl is unsubstituted or substituted by a substituent selected from the group consisting of hydroxyl, carboxyl, guanidino, amino, amido, ester group, sulfonate, chlorosulfinyl, hydroxyphenyl, $C_{1-8}$alkylthio, thiol, $C_{6-10}$aryl and 5- to 10-membered heteroaryl.

2. The method of claim 1, wherein the polar solvent is one selected from the group consisting of water, $C_{1-6}$ aliphatic alcohols, acetonitrile, tetrahydrofuran, N,N-dimethylformamide, dimethyl sulfoxide, N-methylpyrollidone and a combination thereof.

3. The method of claim 1, wherein a weight ratio of the polar solvent to the amino acid ionic liquid is in a range from 10:1 to 1:50.

4. The method of claim 3, wherein the weight ratio of the polar solvent to the amino acid ionic liquid is in a range from 4:1 to 1:20.

5. The method of claim 1, wherein the extracting agent is one selected from the group consisting of benzene, toluene, xylene, $C_{4-8}$ aliphatic alcohols, alkyl phenols, ketones, esters, ethers and a combination thereof.

6. The method of claim 5, wherein the extracting agent is one selected from the group consisting of a mono-substituted phenol having at least three carbon atoms, a di-substituted phenol having at least three carbon atoms, 2-pentanone, 2-hexanone, 2-heptanone, methyl isobutyl ketone, 2,4-pentanedione, ethyl acetate, methyl butyrate, methyl valerate, ethyl ether, butyl ether, isopropyl ether, butanol, isobutanol, tert-butyl alcohol, propanol, isopropanol, hexanol, heptanol, octanol, 2-etyl-1-hexanol, dimethylbutanediol, cyclohexanol and a combination thereof.

7. The method of claim 1, a weight ratio of the extracting agent to the amino acid ionic liquid is in a range from 10:1 to 1:2.

8. The method of claim 7, the weight ratio of the extracting agent to the amino acid ionic liquid is in a range from 6:1 to 1:1.

9. The method of claim 1, wherein the anion of Bronsted acid is selected from the group consisting of sulfate, phosphate, acetate, methylsulfonate, trifluoromethylsulfonate, trifluoroacetate, hexafluorophosphorate, fluoroborate, and a combination thereof.

10. The method of claim 9, wherein the anion of Bronsted acid is sulfate.

11. The method of claim 1, wherein the amino acid ionic liquid is one selected from the group consisting of a glycine sulfuric acid-ionic liquid, an isoleucine sulfuric acid-ionic liquid, an arginine sulfuric acid-ionic liquid, a glutamic acid sulfuric acid-ionic liquid, a tyrosine sulfuric acid-ionic liquid, an aspartic acid sulfuric acid-ionic liquid, a lysine sulfuric acid-ionic liquid, a threonine sulfuric acid-ionic liquid, a phenylalanine sulfuric acid-ionic liquid, a serine sulfuric acid-ionic liquid and a combination thereof.

12. The method of claim 1, wherein a molar ratio of the cation to the anion is in a range from 1:10 to 10:1.

13. The method of claim 1, wherein the ketoxime is one selected from the group consisting of acetone oxime, butanone oxime, benzophenone oxime, acetophenone oxime, cyclopentanone oxime, cyclohexanone oxime, cycloheptanone oxime, cyclooctanone oxime and cyclododecanone oxime.

14. The method of claim 13, wherein a molar ratio of the amino acid ionic liquid to the ketoxime is in a range from 1:10 to 10:1.

15. The method of claim 14, wherein a molar ratio of the amino acid ionic liquid to the ketoxime is in a range from 1:1 to 5:1.

16. The method of claim 1, wherein the organic solvent is an aromatic hydrocarbon.

17. The method of claim 16, wherein the organic solvent is one selected from the group consisting of benzene, toluene, xylene, and a combination thereof.

18. The method of claim 1, wherein the Beckman rearrangement reaction is performed at a temperature ranging from 60 to 150° C. for 0.1 to 10 hours.

* * * * *